(12) United States Patent
Hurson

(10) Patent No.: US 6,431,866 B2
(45) Date of Patent: Aug. 13, 2002

(54) HEAL IN-PLACE ABUTMENT SYSTEM

(75) Inventor: Steven M. Hurson, Yorba Linda, CA (US)

(73) Assignee: Nobel Biocare AB, Gothenburg (SE)

( * ) Notice: Subject to any disclaimer, the term of this patent is extended or adjusted under 35 U.S.C. 154(b) by 0 days.

(21) Appl. No.: 09/853,866

(22) Filed: May 11, 2001

Related U.S. Application Data

(60) Provisional application No. 60/203,333, filed on May 11, 2000.

(51) Int. Cl.⁷ .................................................. A61C 3/00
(52) U.S. Cl. ...................................... 433/172; 433/173
(58) Field of Search ................................ 433/172, 173, 433/174

(56) References Cited

U.S. PATENT DOCUMENTS

| | | |
|---|---|---|
| 4,850,870 A | 7/1989 | Lazzara et al. |
| 4,856,994 A | 8/1989 | Lazzara et al. |
| 5,035,619 A | 7/1991 | Daftary |
| 5,073,111 A | 12/1991 | Daftary |
| 5,145,371 A | 9/1992 | Jorneus |
| 5,145,372 A | 9/1992 | Daftary et al. |
| 5,154,612 A * | 10/1992 | Carlsson et al. ............ 433/173 |
| 5,297,963 A | 3/1994 | Dafatry |
| 5,336,090 A | 8/1994 | Wilson, Jr. et al. |
| 5,338,196 A | 8/1994 | Beaty et al. |
| 5,417,568 A | 5/1995 | Giglio |
| 5,419,702 A | 5/1995 | Beaty et al. |
| 5,431,567 A | 7/1995 | Daftary |
| 5,476,382 A | 12/1995 | Daftary |
| 5,476,383 A | 12/1995 | Beaty et al. |
| 5,492,471 A | 2/1996 | Singer |
| 5,547,377 A | 8/1996 | Daftary |
| 5,599,185 A | 2/1997 | Greenberg |
| 5,651,675 A | 7/1997 | Singer |
| 5,674,069 A | 10/1997 | Osorio |
| 5,674,071 A | 10/1997 | Beaty et al. |
| 5,759,036 A | 6/1998 | Hinds |
| 5,779,481 A | 7/1998 | Aires |
| 5,810,592 A | 9/1998 | Daftary |
| 5,813,858 A | 9/1998 | Singer |
| 5,873,721 A | 2/1999 | Willoughby |
| 5,873,722 A | 2/1999 | Lazzara et al. |
| 5,899,695 A | 5/1999 | Lazzara et al. |
| 6,007,336 A | 12/1999 | Sapkos |
| 6,120,292 A | 9/2000 | Buser et al. |
| 6,126,445 A | 10/2000 | Willoughby |
| 6,129,548 A | 10/2000 | Lazzara et al. |
| 6,155,828 A | 12/2000 | Lazzara et al. |
| 6,227,856 B1 | 5/2001 | Beaty et al. |

FOREIGN PATENT DOCUMENTS

| | | |
|---|---|---|
| GB | 1 291 470 A | 10/1972 |
| WO | WO 99/17676 A | 4/1999 |

OTHER PUBLICATIONS

International Search Report dated Dec. 10, 2001.

\* cited by examiner

*Primary Examiner*—Ralph A. Lewis
(74) *Attorney, Agent, or Firm*—Knobbe, Martens Olson & Bear, LLP

(57) ABSTRACT

A prosthodontic assembly for installing a prosthetic tooth comprises a dental implant and abutment combination and a healing cap. The combination includes an implant body portion and an abutment portion. The implant body portion is located at a distal end of the combination and is configured to lie at least partially below a crest of a patient's jawbone. The abutment portion is located at a proximate end of the combination and is configured to lie at least partially above the crest of the patient's jawbone. The abutment portion comprises a flared portion, a shoulder portion and a final restoration portion. The shoulder portion lies between the flared portion and the final restoration portion. A healing cap includes a body portion having a proximal and a distal end. The body portion defines an inner cavity which is sized and adapted so that the healing cap fits over the final restoration portion. The healing cap further includes a tissue retraction flange at the distal end that extends below the shoulder portion when the healing cap is coupled to the abutment portion.

42 Claims, 14 Drawing Sheets

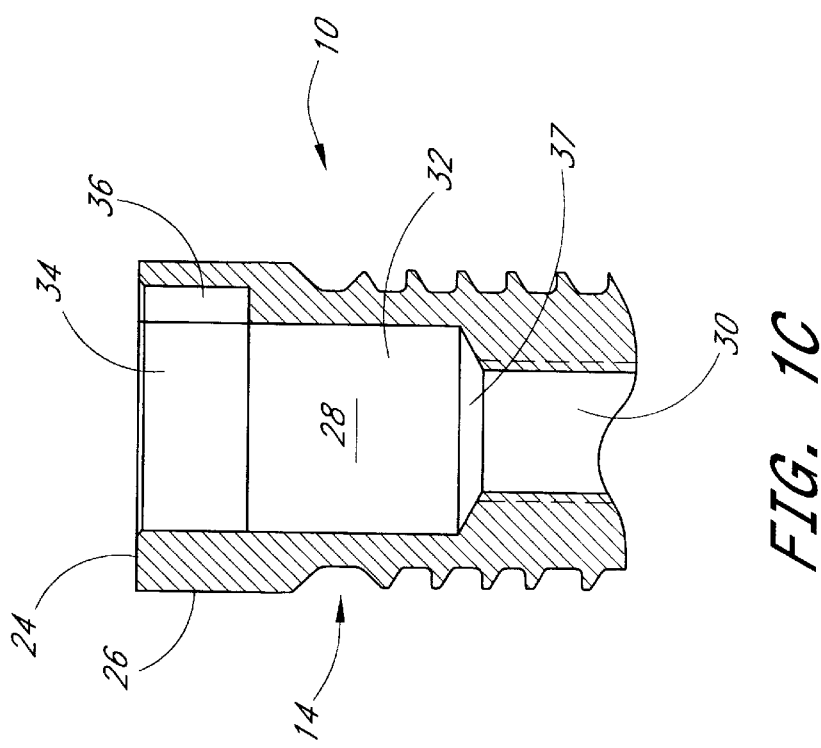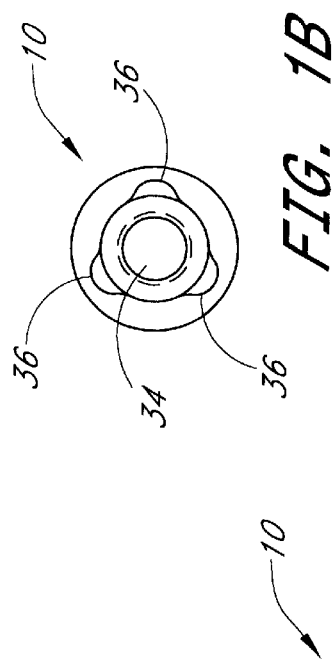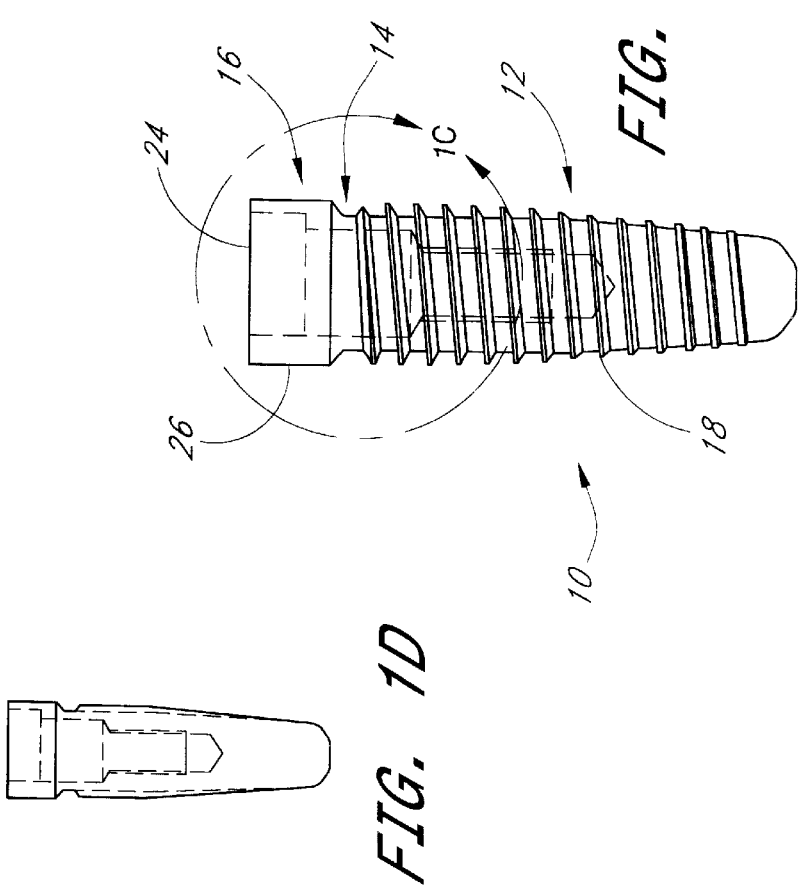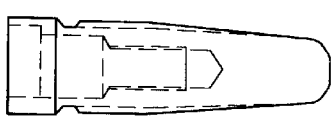

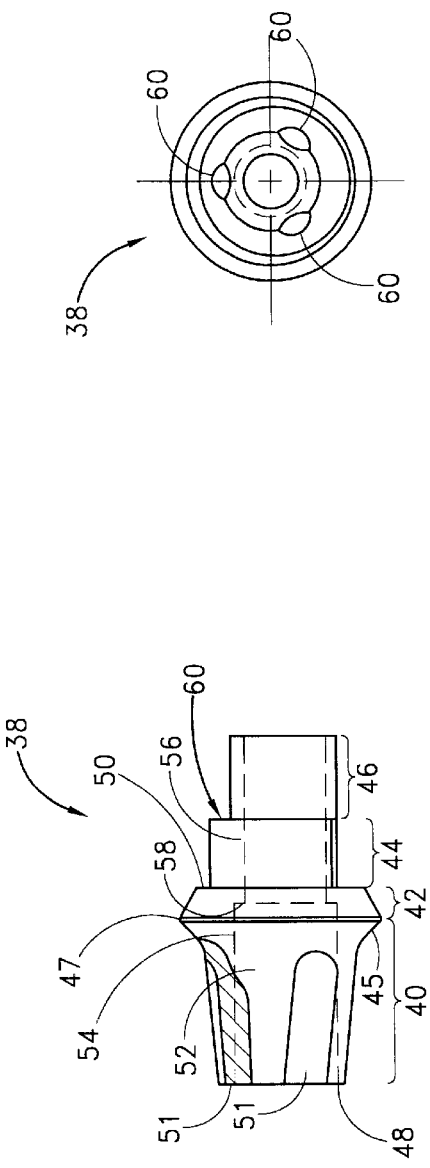
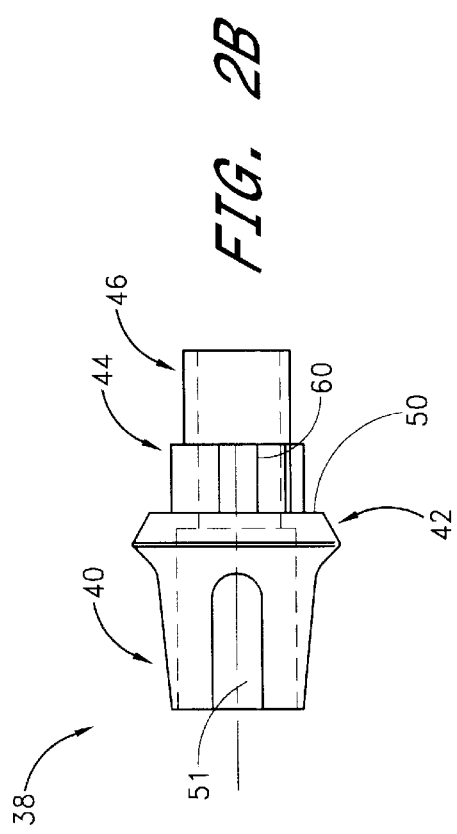
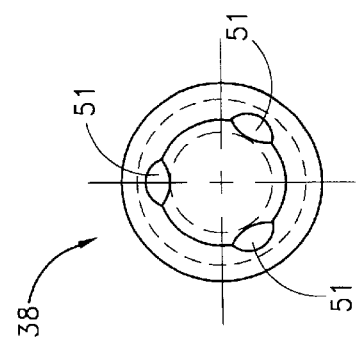

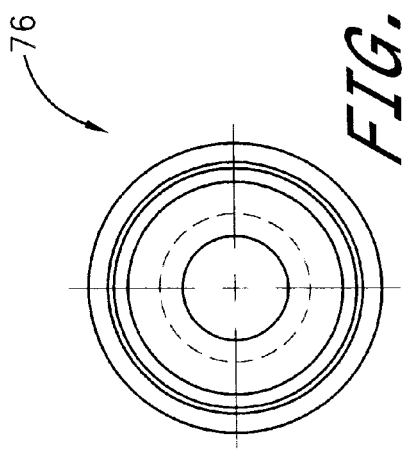
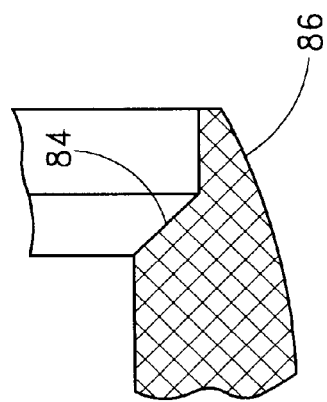
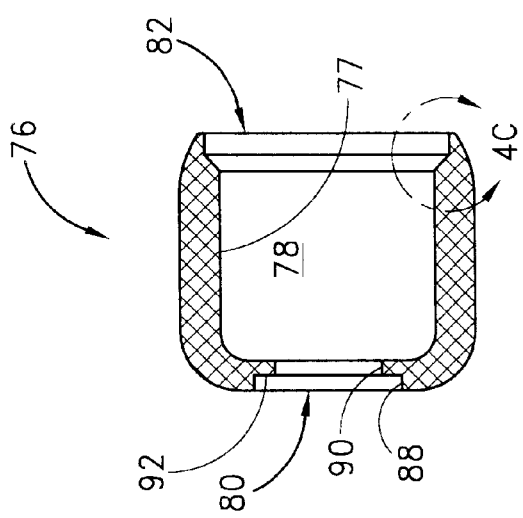

HEAL IN-PLACE ABUTMENT SYSTEM

CROSS REFERENCE TO RELATED APPLICATION

The present application claims priority and benefit under 35 U.S.C. §119(e) of U.S. Provisional Patent Application Ser. No. 60/203,333 filed May 11, 2000, the entire contents of which are expressly incorporated herein.

FIELD OF THE INVENTION

The present invention relates generally to dental implants and, more particularly, to a heal in-place abutment system including a healing cap adapted to be received upon a final abutment.

DESCRIPTION OF THE RELATED ART

Implant dentistry involves the restoration of one or more teeth in a patient's mouth using artificial components. Such artificial components typically include a dental implant and a prosthetic tooth and/or a final abutment that is secured to the dental implant. The process for restoring a tooth can be carried out in three stages.

Stage I involves implanting the dental implant into the bone of a patient's jaw. The oral surgeon first accesses the patient's jawbone through the patient's gum tissue and removes any remains of the tooth to be replaced. Next, the specific site in the patient's jaw where the implant will be anchored is widened by drilling and/or reaming to accommodate the width of the dental implant to be implanted. Then, the dental implant is inserted into the hole in the jawbone, typically by screwing, although other techniques are known for introducing the implant in the jawbone.

The implant itself is typically fabricated from pure titanium or a titanium alloy. Such materials are known to produce osseointegration of the fixture with the patient's jawbone. The dental implant fixture also typically includes a hollow threaded bore through at least a portion of its body and extending out through its proximal end which is exposed through the crestal bone for receiving and supporting the final tooth prosthesis and/or various intermediate components or attachments.

After the implant is initially installed in the jawbone, a cover screw is secured over the exposed proximal end in order to seal the internal bore. The patient's gums are then sutured over the implant to allow the implant site to heal and to allow desired osseointegration to occur. Complete osseointegration typically takes anywhere from four to ten months.

During stage II, the surgeon reaccesses the implant fixture by making an incision through the patient's gum tissues. The cover screw is then removed, exposing the proximal end of the implant. The interior of the implant is thoroughly cleaned and dried. The surgeon then attaches a temporary healing abutment or a final abutment to the implant. Typically, the healing or final abutment includes a threaded post, which is screwed directly into the hollow threaded bore of the implant. To accurately record, the position the orientation and the shape of the final abutment, the surgeon can take a mold or impression of the patient's mouth . The impression is used to create a plaster model or analogue of the mouth and the abutment and provides the information needed to fabricate the prosthetic replacement tooth and any required intermediate prosthetic components. Stage II is typically completed by securing a protective cap to the abutment with temporary cement. Alternatively, a conventional temporary restoration can be attached to the abutment.

Stage III involves fabricating and placement of a cosmetic tooth prosthesis to the implant fixture. The plaster analogue provides laboratory technicians with a model of the patient's mouth and the final abutments. Based on this model, the technician constructs a final restoration. The final step in the restorative process is attaching the final restoration to the abutment.

SUMMARY OF THE INVENTION

In accordance with one embodiment, the present invention provides for a prosthodontic assembly for installing a prosthetic tooth. The assembly comprises a dental implant and abutment combination and a healing cap. The combination includes an implant body portion and an abutment portion. The implant body portion is located at a distal end of the combination and is configured to lie at least partially below a crest of a patient's jawbone. The abutment portion is located at a proximate end of the combination and is configured to lie at least partially above the crest of the patient's jawbone. The abutment portion comprises a flared portion, a shoulder portion and a final restoration portion. The shoulder portion lies between the flared portion and the restoration portion. A healing cap includes a body portion having a proximal and a distal end. The body portion defines an inner cavity which is sized and adapted so that the healing cap fits over the final restoration portion. The healing cap further includes a tissue retraction flange at the distal end that extends below the shoulder portion when the healing cap is coupled to the abutment portion.

In accordance with another embodiment, the present invention provides for a method for installing a prosthetic tooth. The method comprises inserting a distal end of a body portion of a dental implant and abutment combination into a patient's jawbone during a first stage surgery, coupling a healing cap to an abutment portion of the combination, during first stage surgery, such that a tissue retraction flange of the healing cap extends below a shoulder portion of the abutment portion, removing the healing cap from the abutment portion during a second stage surgery, and taking an impression of the combination during the second stage surgery after the healing cap has been removed from the abutment portion.

In accordance with yet another embodiment, the present invention provides for healing cap for combination with a dental implant in a method of installing a prosthetic tooth. The healing cap comprises a body having a proximal end, a distal end, and a cavity thereon, sized and adapted such that the distal end will fit over an abutment, and into a mounted position with respect to the abutment. The abutment has a radially outwardly extending shoulder. The body further includes a tissue retraction surface, which extends distally of the shoulder when the body in the mounted position.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

These and other features of the invention will now be described with reference to the drawings of the preferred embodiments, which are intended to illustrate and not to limit the invention, and in which:

FIG. 1A is a side view of a dental implant having certain features and advantages according to the present invention;

FIG. 1B is a top plan view of part of the dental implant of FIG. 1A;

FIG. 1C is a cross-sectional view of the dental implant of FIG. 1A;

FIG. 1D is a side view of a modified dental implant without threads;

FIG. 2A is a side view of a final abutment having certain features and advantages according to the present invention;

FIG. 2B is another side view of the final abutment of FIG. 2A;

FIG. 2C is a top plan view of the final abutment of FIG. 2A;

FIG. 2D is a bottom plan view of the final abutment of FIG. 2A;

FIG. 4A is a cross-sectional view of a healing cap having certain features and advantages according to the present invention;

FIG. 4B is a bottom plan view the healing cap of FIG. 4A;

FIG. 4C is a is a closer view of a section of the healing cap of FIG. 4A;

DETAILED DESCRIPTION OF THE PREFERRED EMBODIMENTS

Figure 1E:
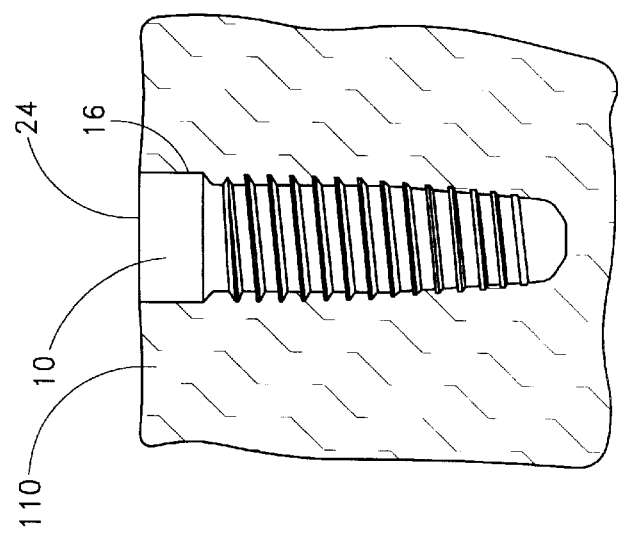
FIG. 1E–G illustrate the implant of FIGS. 1A–1C inserted into a patient's jawbone at three different positions with respect to a patients jawbone.

FIGS. 1–7 illustrate the primary components of a heal in-place abutment system having certain features and advantages according to the present invention. With initial referenced to FIGS. 1A–1C, a preferred embodiment of a dental implant 10 will be described. The implant 10 is preferably sized and dimensioned to receive and support one or more dental attachments or components, which will be described in detail below. In particular, the dental implant 10 is sized and dimensioned to support a final abutment to which a final restoration can be attached. The implant 10 is preferably made of a dental grade titanium alloy, although other suitable materials can also be used.

As best seen in FIG. 1A, the implant 10 includes a body portion 12, a neck 14, and a collar 16. The body portion 12 is preferably tapered and includes threads 18 that mate to a preformed threaded hole or osteotomy formed in the patient's jawbone (not shown). However, it should be appreciated that the body portion 12 can also be configured so as to be self-tapping. It should also be appreciated that although the illustrated body portion 12 is tapered or conical, the body portion 12 can be substantially cylindrical. Finally, it should be appreciated that the body portion 12 can be unthreaded, as shown in FIG. 1D, if the surgeon prefers to use an unthreaded implant 10.

The collar 16 of the implant is substantially cylindrical and has a top surface 24 that is substantially flat. The collar 16 is defined in part by a vertical side wall 26 that, in the preferred embodiment, is approximately 2 millimeters in axial length.

The collar 16 forms a "variable placement zone". The length and configuration the variable placement zone allows for "variable positioning" of the dental implant 12. That is, the surgeon can vary the height of the implant 10 with respect to the crest of the jawbone 110. For example, the surgeon can submerge the collar 16 into the jawbone such that the top surface 24 lies flush with the crest of the jawbone (FIG. 1E).

Figure 1F:
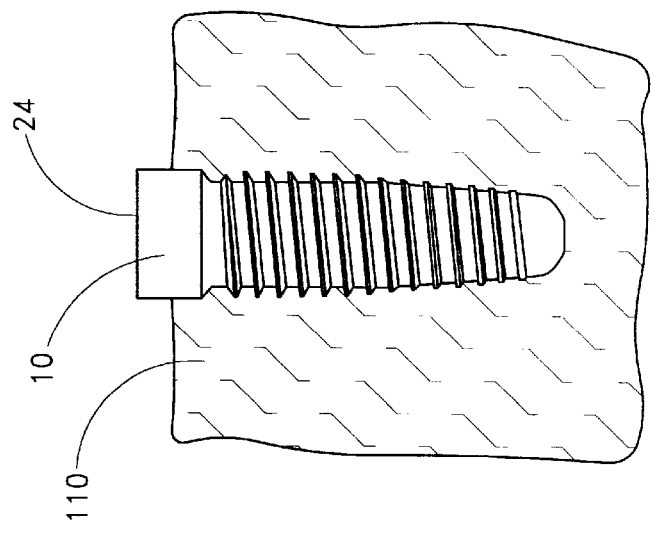
Figure 1G:
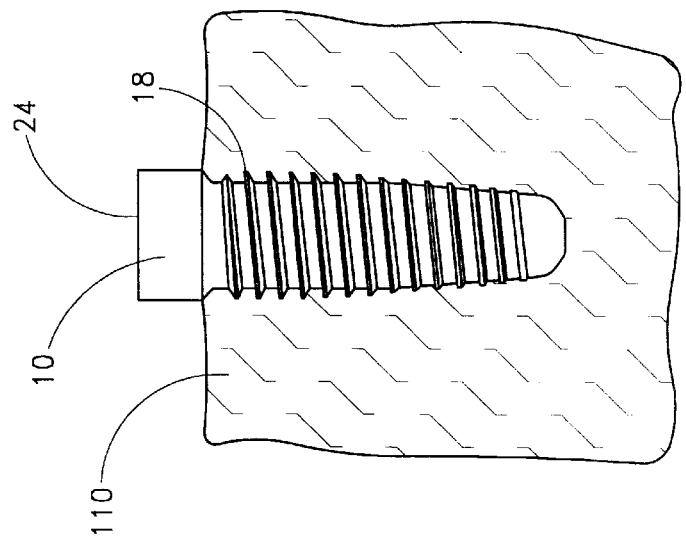

Alternatively, as shown in FIG. 1F, the surgeon can place the top surface 24 of the implant 10 slight above the jawbone for esthetics (e.g., level with the alveolar crest). In another embodiment (FIG. 1G), the implant 10 can be placed supra-crestally. That is, the top surface 24 of the implant 10 can positioned above the crest of the jawbone without exposing the threads 18 of the body region 12.

It should, however, be noted that several advantages of the present invention can be achieved with an implant 10 that (i) does not include a variable placement zone or (ii) includes variable placement zone that is smaller or larger than the preferred embodiment. For example, several advantages of the present invention can be achieved with an implant without the neck 14 and/or the collar 16. Similarly, the neck 14 and/or collar 16 can have dimensions that are smaller or larger than the illustrated embodiment. However, the illustrated embodiment, with the neck region 14 and collar 16, is preferred because it best allows for the flexibility described above.

As best seen in FIG. 1C, the implant 10 also includes an internal socket 28.

The internal socket 28 preferably includes a threaded chamber 30, a post receiving chamber 32, and an anti-rotation chamber 34.

With reference to FIGS. 1B and 1C, the anti-rotation chamber 34 has a central portion having a substantially cylindrical shape. The anti-rotation chamber 34 further includes one or more radially extending portions rotational engagement portions each comprising a channel or lobe 36 extending from the top surface 24 to the bottom of the indexing chamber 34. In the illustrated embodiment, three engagement portions 35 are provided, each having a substantially half circular shape. As best seen in FIG. 1B, the channels 36 are situated and evenly spaced around the perimeter of the indexing region 34. Each channel 36 may be spaced 120 degrees apart from each other channel 36. The anti-rotation chamber 34 is designed to mate with a corresponding anti-rotation region formed on various mating components, such as, for example, a final abutment. The anti-rotation chamber 34 primarily serves to prevent relative rotation between the mating component and the implant 10.

It should be appreciated that several advantages of the present inventions can be achieved with an implant that does not include the anti-rotation chamber 34. However, the implant 10 preferably includes the anti-rotation chamber 34 because it helps to prevent the relative rotation between the mating components (e.g., a final abutment) and the implant 10. It should also be appreciated that the anti-rotation chamber 36 can be formed into a wide variety of other suitable shapes that may be used with efficacy, giving due consideration to the goals of providing anti-rotation of mating components.

For example, the anti-rotation chamber 36 could comprise a hexagonal recess or protrusion that is situated on the top surface 18 of the implant 10. Nevertheless, the illustrated arrangement is preferred because it provides optimal clinical efficacy, ease of use and also minimizes stress concentrations within the anti-rotation chamber 34.

The post-receiving chamber 32 lies between the anti-rotation chamber 34 and the threaded chamber 30. The post-receiving chamber 32 may have a diameter that is less than the diameter of the anti-rotation chamber 36. The post-receiving receiving chamber 32 may include a chamfered region 37, which is adjacent the threaded region 30. As will be explained below, the post-receiving chamber 32 is sized and dimensioned to receive a post that is attached to a mating dental component. The post and the post-receiving chamber 32 provide lateral support, which prevents the mating component from tipping off the implant. However, it should be appreciated that several advantages of the present invention can be achieved with an implant 10 formed without the post-receiving chamber 32.

The threaded chamber 30 lies below the post-receiving chamber 32. The threaded chamber 30 is threaded and has a diameter that may be less than the post-receiving chamber 32.

FIGS. 2A–2D illustrate a preferred embodiment of a final abutment 38 having certain features and advantages in accordance to the present invention. The final abutment 38 is preferably sized and dimensioned to mate with the implant 10 described above. It is also sized and dimensioned to support a final restoration (see FIG. 9). The final abutment 38 is preferably made of a dental grade titanium alloy, although other suitable materials can be used.

As best seen in FIG. 2A, the outer surface of the final abutment 38 preferably includes an upper region 40, a flared region 42, an anti-rotation region 44, and a post 46. In the preferred embodiment, the upper region 40 is substantially smooth and tapered. The upper region 40 also has a top surface 48 that is substantially flat.

Towards the bottom of the upper region (i.e., the portion nearest the flared region 42) is a flared portion 45 that flares outward towards a shoulder 47. The flared region 42 extends from the ridge and connects the upper region 40 to a bottom surface 50, which is substantially flat.

Figure 8:
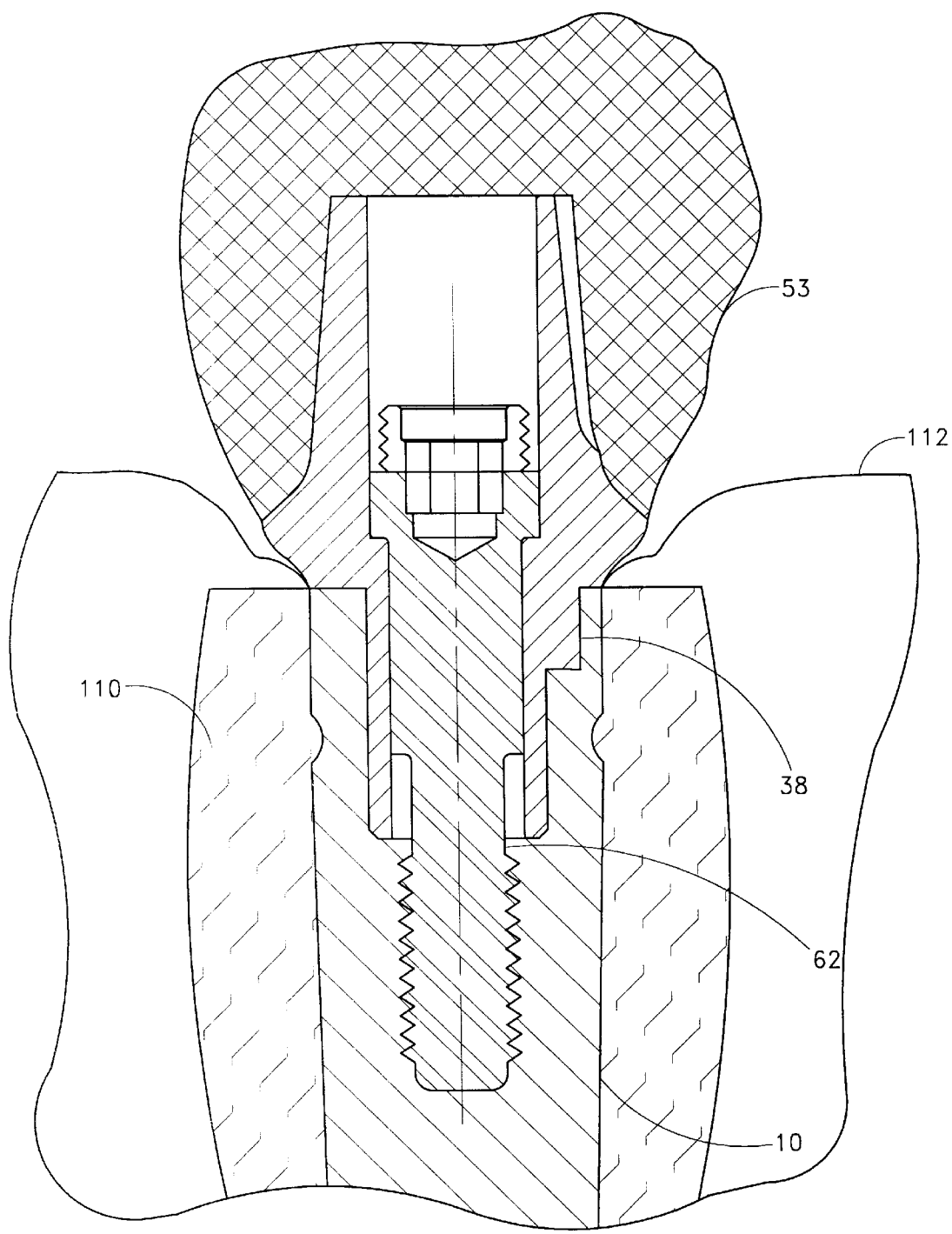
FIG. 8 is a cross-sectional view of the implant inserted into a patients jawbone with the final abutment, the coupling screw, and a final restoration coupled to the implant.

The upper region 40 also preferably includes a plurality of grooves 51. These grooves 51 help orient and prevent the rotation of a final restoration 53 (FIG. 8). Accordingly, the final restoration 53 has an inner surface that matches or engages the shape of the upper region 40 of the final abutment 38. However, those skilled in the art will readily appreciate that the upper region 40 and the grooves 51 can be formed into a variety of other shapes that can also provide an anti-rotational interface between the final restoration 54 and the final abutment 38. It should be appreciated that although the illustrated cross-sections of the upper region and flared region are round in modified arrangements the cross-sections can be nonround. For example, the cross-section of the upper region and flared region can have a non-round cross-section that resembles the cross-section of a natural tooth.

To permanently secure the final restoration 53 , cement can be applied to the upper region 40 of the final abutment 38. Alternatively, the final restoration 52 can be coupled to the final abutment 38 by a screw (not shown). In such an arrangement, a screw hole (not shown) can be provided on the side of the final abutment 38.

As best seen in FIG. 2A, the final abutment 38 advantageously includes an inner bore 52 that extends through the center of the final abutment 38. The inner bore 52 is preferably defined by a first and second region 54, 56. The diameter of the first region 54 is preferably slightly larger than the diameter of the second region 56. Accordingly, a seat 58 is formed between the first and second regions 54, 56. The seat 58 supports a coupling screw 60 (see FIG. 3A), which will be described in detail below. Optionally, the second region 56 can include internal capture threads (not shown).

With continued reference to FIG. 2A, the diameter of the bottom surface 50 is approximately equal to the diameter of the top surface 24 of the implant 10. Extending from the bottom surface 50 is the anti-rotation region 44, which is sized and dimensioned to fit within the anti-rotation chamber 36 of the implant. Accordingly, as best seen in FIGS. 2B and 2D, the anti-rotation region 44 is substantially cylindrical and includes three protrusions 60. The protrusions 60 preferably extend along the entire length of the anti-rotation region 44 and have a half circular shape. The protrusions 60 are arranged around the perimeter of the indexing region 44 approximately 120 degrees apart relative to the center axis of the final abutment 38.

As with the anti-rotation chamber 36 of the implant 10, it should be appreciated that several features and advantages of the present invention can be achieved with a final abutment 38 does not include the anti-rotation region 44. However, it is preferred that the abutment 38 include the anti-rotation 44 because it helps to prevent relative rotation between the implant 10 and the final abutment 38. It should also be appreciated that the anti-rotation region 44 can be formed into a wide variety of other suitable shapes that may be used with efficacy to prevent rotation of the implant 10 and the final abutment 38.

Below the indexing region 44 is the post 46. The post 46 is substantially cylindrical and is sized and dimensioned to fit within the post-receiving chamber 32 of the implant 10. As mentioned above, the post 36 provides lateral support to the final abutment 38 when it is placed upon the implant 10. However, it should be appreciated that several advantages of the present invention can be achieved with a final abutment 38 that does not include a post 45.

Figure 3A:
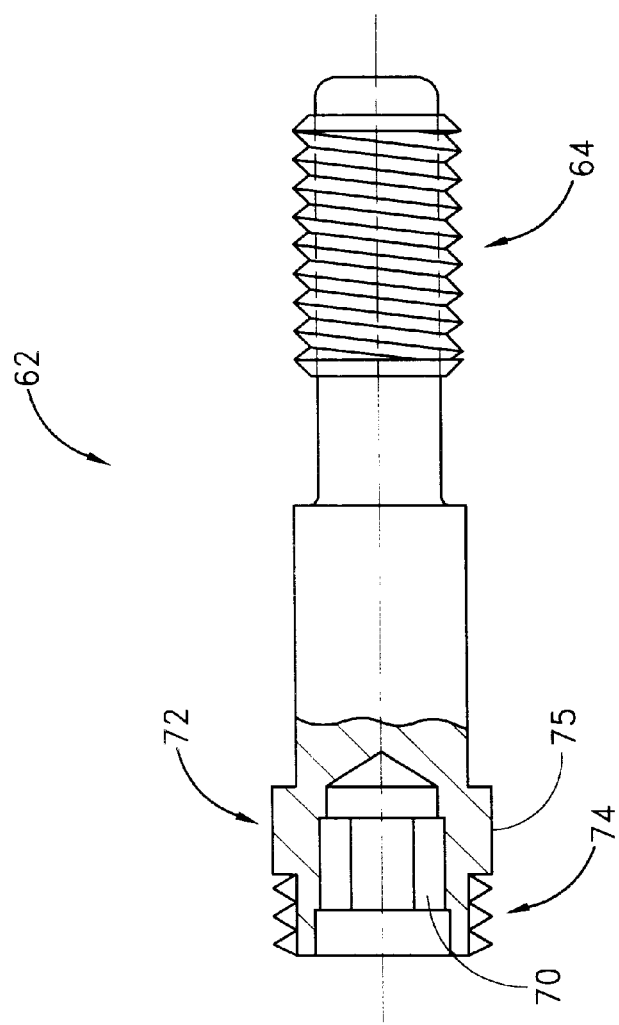
FIG. 3A is a partial cross-sectional side view of a coupling screw having certain features and advantages according to the present invention.
Figure 3B:
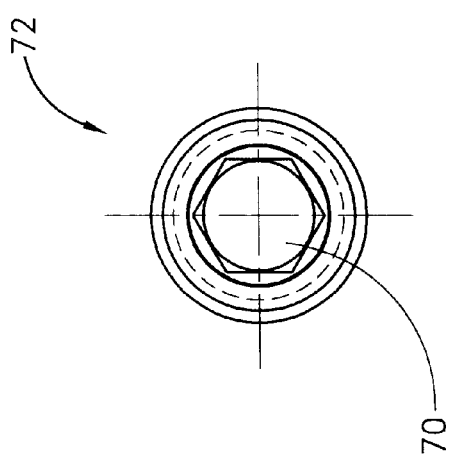
FIG. 3B is a top plan view of the coupling screw of FIG. 3A.

Turning now to FIGS. 3A and 3B, the coupling screw 62 is sized and dimensioned to extend through the inner bore 52 of the final abutment 38 and to couple the final abutment 38 to the implant 10. As with the final abutment 38, the coupling screw 60 is preferably made of a dental grade titanium alloy. However, other suitable materials can be used.

The coupling screw 62 has an externally threaded lower region 64. The threaded lower region 64 is sized and dimensioned to engage the threads of the threaded chamber 30 of the implant 10 (see FIG. 1C). The threaded lower region 64 can also engage capture threads that can be formed on the second region 56 of the final abutment 38. In such an arrangement, the coupling screw 62 engage the capture threads so that the coupling screw 62 does not become disassociated as the final abutment 38 is transferred and fitted to the patient's mouth.

The coupling screw 62 also advantageously includes a hexagonal recess 70 located within a head 72 of the screw 60. The hexagonal recess 70 allows for the insertion of a hexagonally shaped tool such as a conventional Allen® wrench, which can be used to apply rotational force to the coupling screw 62. The head 72 also advantageously includes outer threads 73, which are formed on the outer surface 75 of the head 72. The purpose and function of the outer threads 73 will be described below. Alternatively, the threads 73 can be formed internally within the recess 70.

FIGS. 4A–4C illustrate a healing cap 76 having certain features and advantages according to the present invention. The healing cap 76 may be made of a synthetic polymer, such as, for example, polyester or Nylon. However, it should be appreciated that other suitable materials can also be used. The healing cap 76 is preferably white or close to natural tooth color so that it has a natural appearance when it is placed in the patient's mouth.

Figure 6:
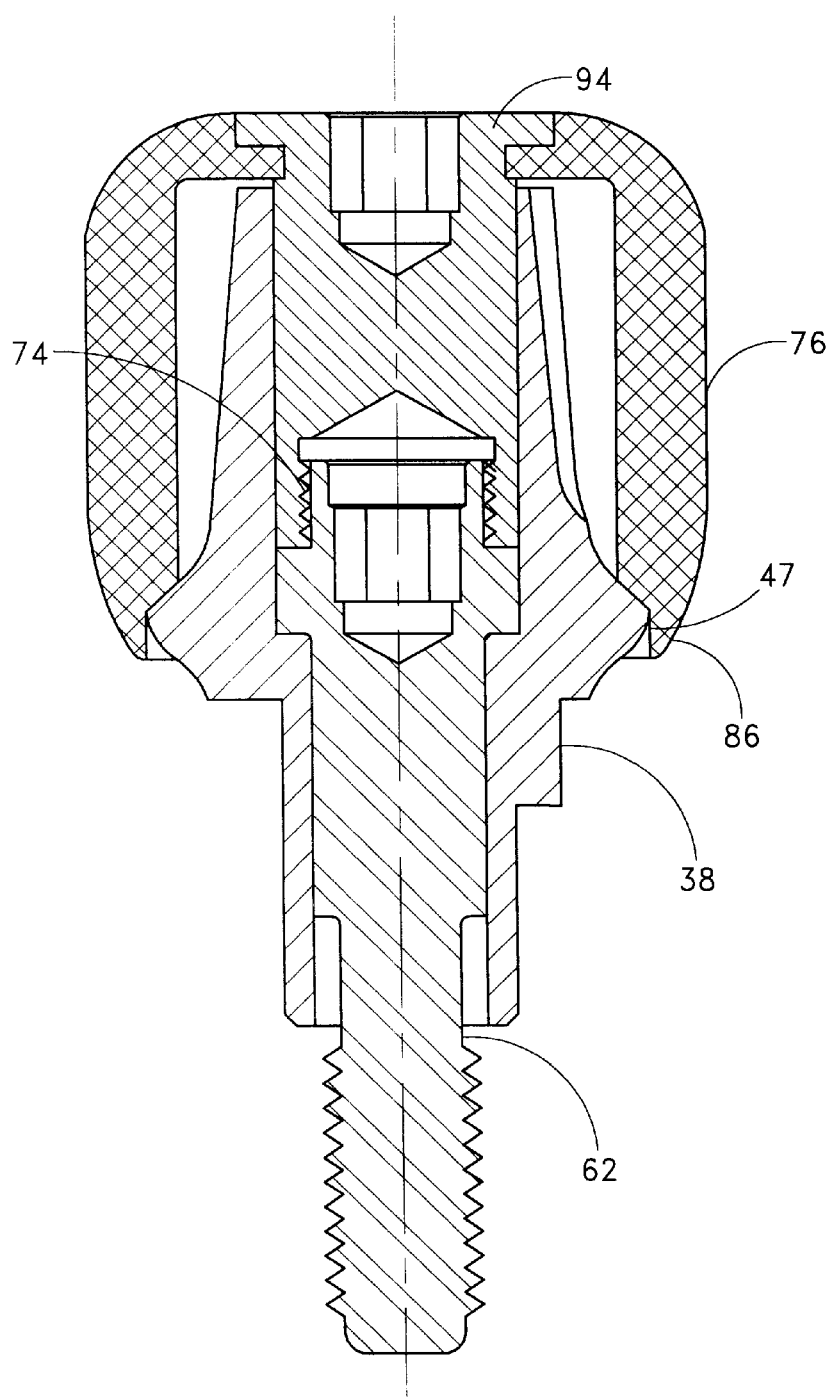
FIG. 6 is a cross-sectional view of the final abutment, the coupling screw, the healing cap and the healing cap screw coupled together.

The healing cap 76 includes an inner surface 77 which defines an internal cavity 78. The inner surface 77 also defines a top opening 80 and a bottom opening 82. The inner surface 77 is sized and dimensioned such that the that healing cap fits over the upper region 40 of the final abutment 38 as best seen in FIG. 6. With particular reference to FIG. 4C, the inner surface 77 preferably includes a stop for limiting advance of the healing cap 76 onto the abutment 38, such as, a base surface 84 that is sized and dimensioned to rest against the flanged portion 45 of the final abutment 38.

With continued reference to FIG. 4C, the healing cap 76 also preferably includes a tissue retraction flange 86. The tissue retraction flange 86 is sized and dimensioned such that when the healing cap 76 is placed upon the final abutment 38 it extends beyond at least the upper limit of the shoulder 47 of the final abutment 38. The purpose and function of the tissue retraction flange 86 will be described below.

With reference to FIG. 4B, the top opening 80 is preferably defined by top and bottom portions 88, 90. The diameter of the top portion 88 is slightly larger than the diameter of the second portion 90. Accordingly, a seat 92 is formed between the first and second portions 88, 90. The seat 92 provides support for a healing cap screw 94 (see FIGS. 5A–C). Alternatively, and/or in addition, the opening 80 may be flared or chamfered to provide a flared seating surface.

As with the final abutment 38, it should be appreciated that although the illustrated cross-sections of the healing cap 76 are round in modified arrangements the cross-sections can be non-round. For example, the cross-sections can have a non-round cross-section that resembles the cross-section of a natural tooth.

Figure 5C:
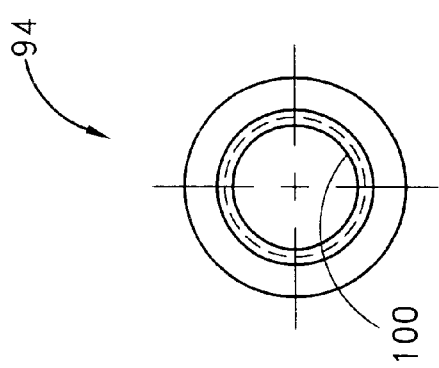
FIG. 5C is a bottom plan view of the healing cap screw of FIG. 5A.
Figure 5A:
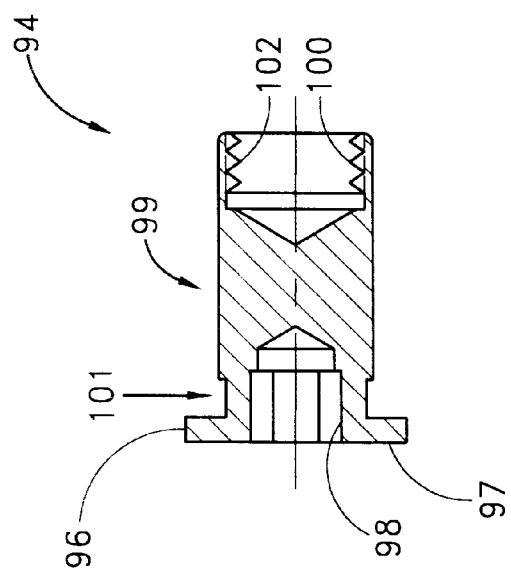
FIG. 5A is a cross-sectional view of a healing cap screw having certain features and advantages according to the present invention.
Figure 5B:
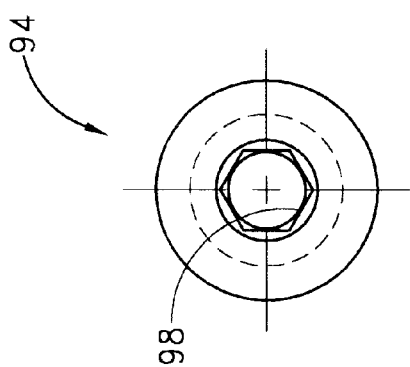
FIG. 5B is a top plan view of the healing cap screw of FIG. 5A.

Turning now to FIGS. 5A–C, the healing cap screw 94 will now be described.

The healing cap screw 94 is sized and dimensioned so as extend through the healing cap 76 and to couple the healing cap 76 to the final abutment 38. The healing cap screw 94 is preferably made of a dental grade titanium alloy; although, other suitable materials can be used.

As best seen in FIG. 5A, the healing cap screw 94 includes a flange 96, an upper hexagonal recess 98, a barrel 99 and a lower recess 100. The flange 96 preferably has a diameter that is slightly smaller than the diameter of the upper portion 88 of the healing cap 76. Furthermore, as seen in FIG. 6, the flange 96 is preferably sized and dimensioned such that the top surface 97 of the flange 98 sits flush with the healing cap 76.

The hexagonal recess 98 extends through the flange 96 and allows for the insertion of a hexagonally shaped tool such as a conventional Allen® wrench, which can be used to rotate the healing cap screw 94.

The threaded recess 100 is positioned on the lower end of the healing cap screw 94. The threaded recess 100 includes threads 102 that are sized and dimensioned to match the outer threads 74 on the head 72 of the coupling screw 62. Accordingly, as best seen in FIG. 6, the healing cap screw 94 extends through the healing cap 76 and can engage the outer threads 74 of the coupling screw 62.

Preferably, the barrel 99 has a diameter that is slightly larger than the inner diameter of the bottom portion of the healing cap 76. The barrel 99 preferably includes a groove 101, which is located below the flange 96 and has a diameter that is slightly smaller than the inner diameter of the bottom portion 90 of the healing cap. As such, the healing cap screw 94 can be press-fit into the healing cap 76 such that the bottom portion 90 fits into the groove 101 and the top portion 97 is flush with the top of the healing cap 76. In this manner, the healing screw 94 is captured by the healing cap 76 and can rotate freely inside the healing cap 76. Of course, in a modified arrangement, the healing cap screw 94 can be configured without the capture feature as shown in FIG. 6.

In use, the surgeon first places the implant 10 (see FIG. 7) into the patient's jawbone during Stage I surgery. The surgeon then places the healing cap 76 over the final abutment 38 and uses the captured healing cap screw 94 to couple the healing cap 76 to the final abutment 38. Specifically, the surgeon rotates the healing cap screw 94 so that the inner threads 102 engage the outer threads 74 of the coupling screw 62. Accordingly, the healing cap 76 is held securely against the final abutment 38. As will be explained in more detail below, the healing cap 76 helps to control the healing and growth of the patient's gum tissue around the implant site. The healing cap 76 also improves the appearance of the patient's mouth and provides the patient with a temporary chewing surface. If desired, the healing cap 76 can also be used to support a temporary restoration and/or may itself be shaped in the form of a temporary restoration.

The patient then returns home and the implant is allowed to osseointegrate with the jawbone and the patient's gums are allowed to heal. Once the implant osseointegrates and the gums heal, the patient returns to the surgeon who takes an impression of the patient's mouth. The surgeon loosens the healing cap screw 94 and removes the healing cap 76 from the final abutment 38. At this point, the surgeon takes the impression of the patient's mouth to record the position, orientation and shape of the final abutment within the mouth.

The impression is used to make a model of the patient's mouth and to form the final restoration. As mentioned above, the final restoration 53 (see FIG. 8) has an inner surface that matches the upper region 40 of the final abutment 38. Accordingly, in a final procedure, the surgeon can attach the final restoration 53 by slipping it onto the final abutment 38 cementing it in place and/or securing it with a screw.

In a modified arrangement, the final abutment 38 can be attached during a traditional Stage II surgery. In such an arrangement, an impression of the final abutment 38 can also be made during Stage II before the healing cap 76 is attached to the final abutment 38.

Figure 7:
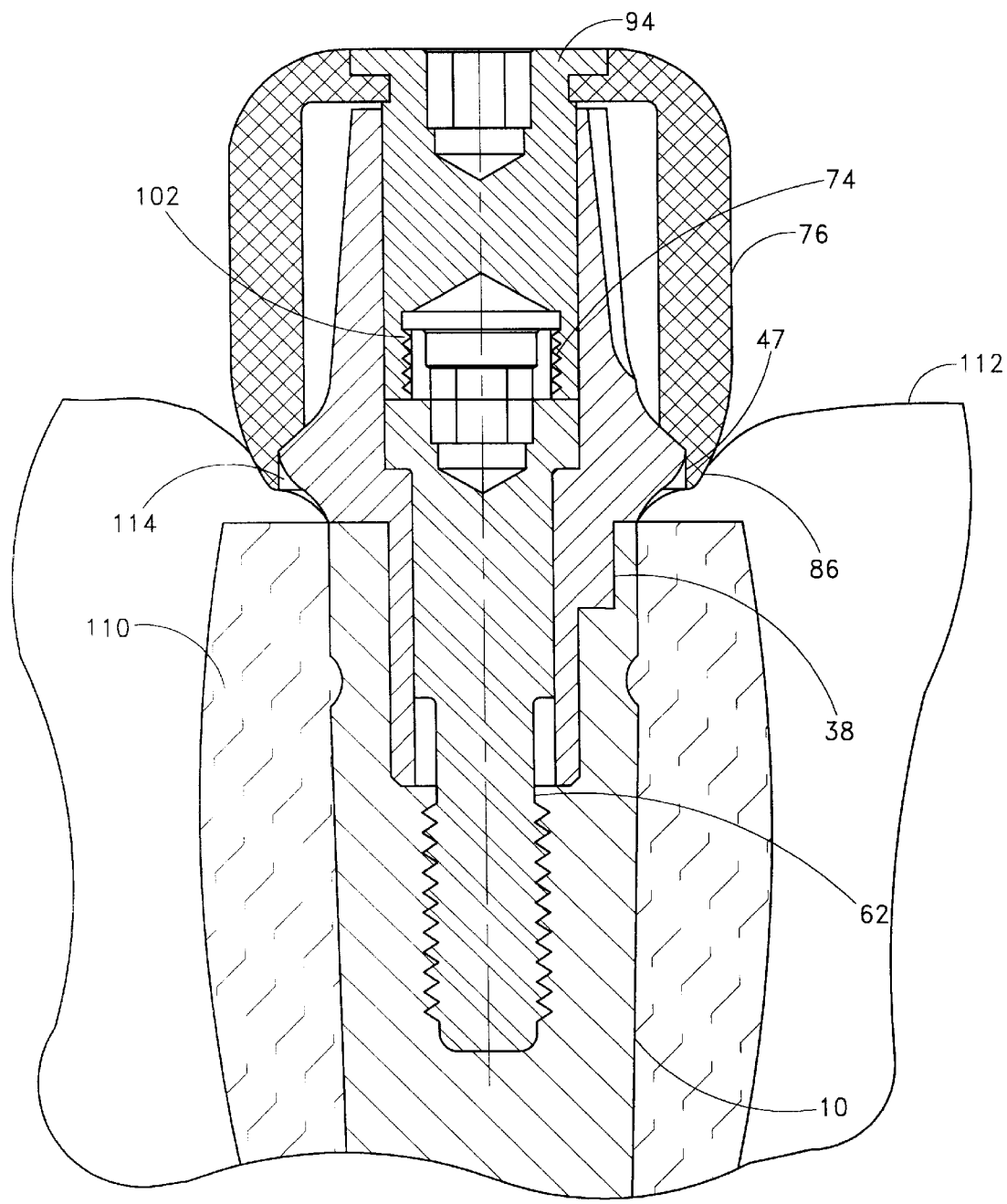
FIG. 7 is a cross-sectional view of the implant inserted into a patients jawbone with the final abutment, the coupling screw, the healing cap, the healing cap screw, and the implant coupled to the implant.
Figure 9:
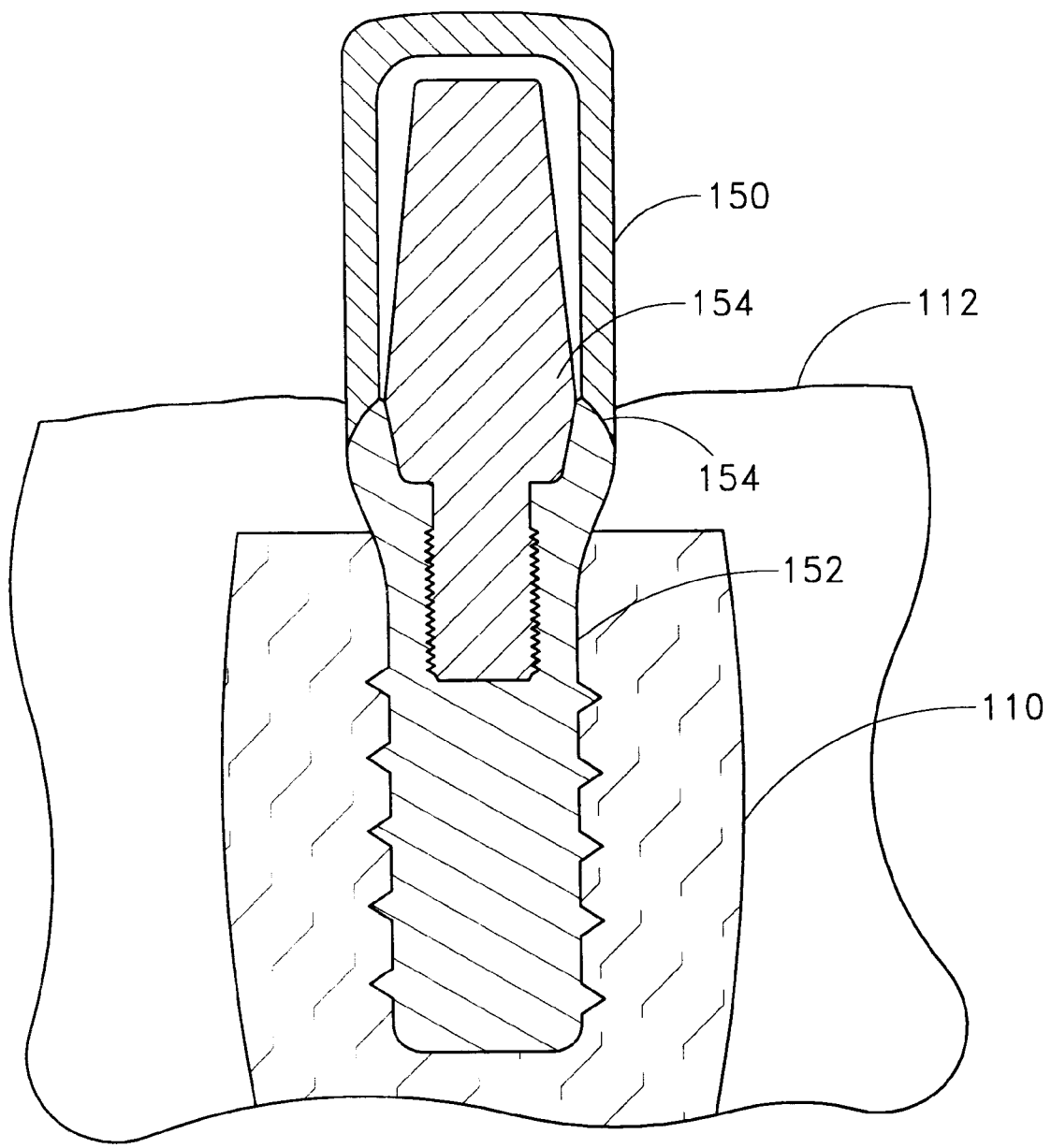
FIG. 9 is a cross-sectional view of a healing cap, a final abutment and an implant according to the prior art.

As best seen in FIG. 7, one of the features and advantages of the present invention is the way the tissue retraction flange 86 controls the healing and growth of the patient's gum tissue 112 around the final abutment 38. In comparison, FIG. 9 illustrates a prior art protection cap 150, implant 152 and final abutment 154. The implant 152 includes a shoulder region 156. The protection cap 150 rests upon the shoulder region 156. Because, the prior art healing cap 150 does not extend beyond the shoulder region 153, the gum tissue 112 during a healing period grows near and above the shoulder region 156. This may causes several problems. For example, when the protection cap 150 is removed, the gum tissue 112 tends to relax and fall over the shoulder region 156. When an impression is taken of the final abutment 154, this fallen gum tissue can compromise the accuracy of the impression. Moreover, if an impression cap such as the one disclosed in U.S. Pat. No. 5,688,123 is used, the fallen gum tissue can become pinched between the impression cap and the shoulder region 156 when the impression cap is snapped over the shoulder region 156. This can cause discomfort to the patient. In addition, when a final restoration is attached to the final abutment 154 and implant 152, the gum tissue can also become pinched in between the final restoration and the shoulder region 156.

In contrast, as shown in FIG. 7, the preferred embodiment of the healing cap 76 includes a tissue retraction flange 86 that extends below the shoulder 47 of the final abutment 38. The tissue retraction flange 86 pushes the gum tissue 112 down and away from the shoulder 47. The tissue retraction flange 86 also pushes the gum tissue 112 laterally away from the shoulder 47. Accordingly, a gap 114 is formed between the gum tissue 112 and the shoulder 47 of the final abutment 38. Thus, when the healing cap 76 is removed, the gum tissue is less likely to fall over the shoulder 47. This arrangement tends to prevent patient's gums from falling over the shoulder 47 of the abutment when (i) the impression is taken, (ii) an impression cap is being attached to the abutment and/or when the final restoration 53 is attached to the abutment 38. This results in more accurate impressions and minimal discomfort to the patient.

The tissue retraction flange 86 sized and dimensioned to hold the gum tissue 112 far enough away from the shoulder 47 to achieve some or all the results described above. Generally, the tissue retraction flange 86 holds the gum tissue 112 at least about 0.25 millimeters below the shoulder, in some embodiments about 0.5 millimeters, in other embodiments 1 millimeter or greater.

Figure 10:
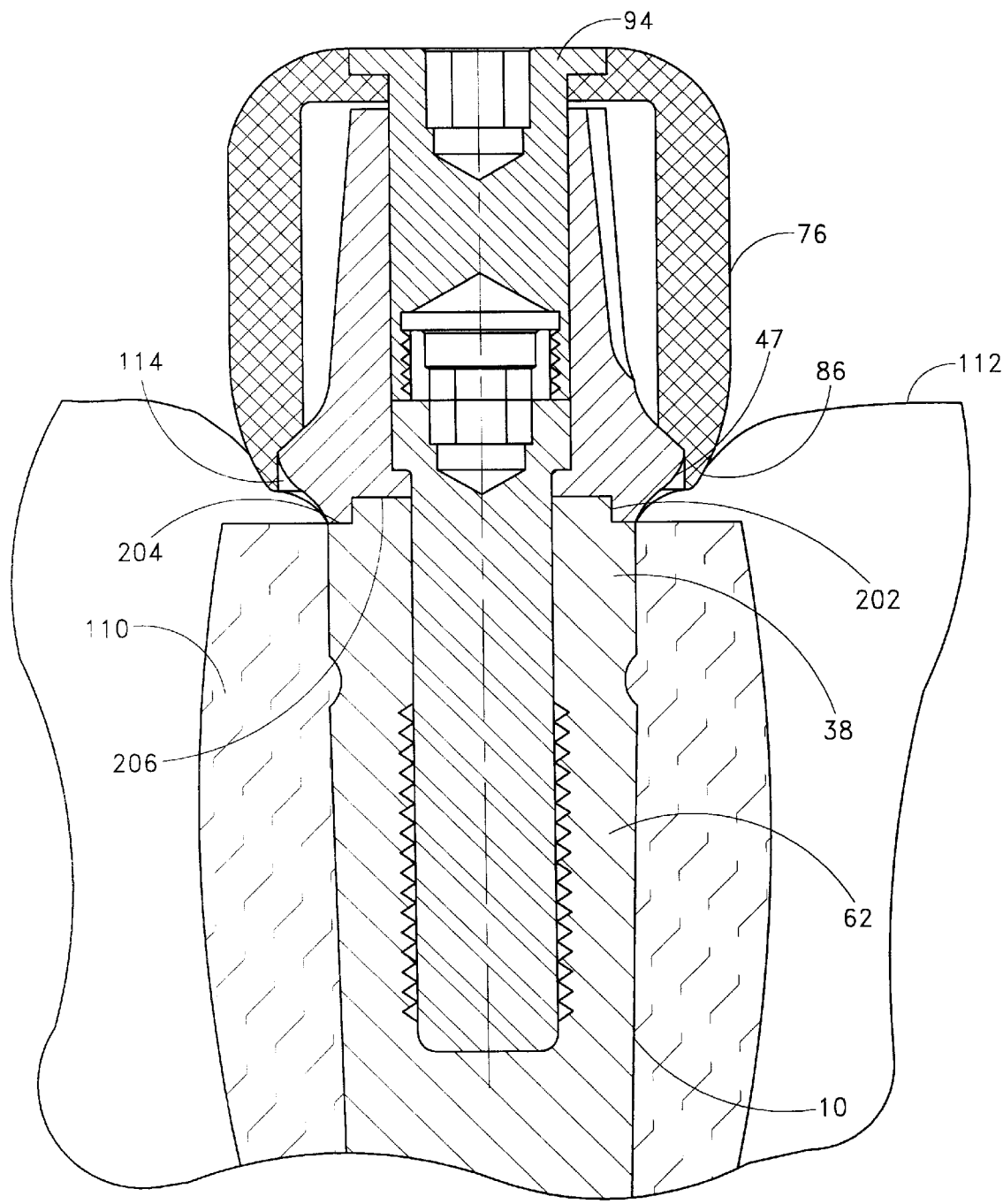
FIG. 10 is another embodiment of a heal in-place abutment system having certain features and advantages according to the present invention.

FIG. 10 illustrates a modified embodiment of a heal in-place abutment system having certain features and advantages according to the present invention. In this embodiment, the final abutment 38 is configured to mate with a conventional implant 200, which includes a hexagonal protrusion 202 situated on the top 204 surface 18 of the implant 200. Correspondingly, the final abutment 38 includes a hexagonal recess 206 that is configured to mate with the hexagonal protrusion 202 of the implant 200. One of the advantages of this embodiment of the heal-in place abutment system is that it utilizes a conventional implant 10.

Figure 11:
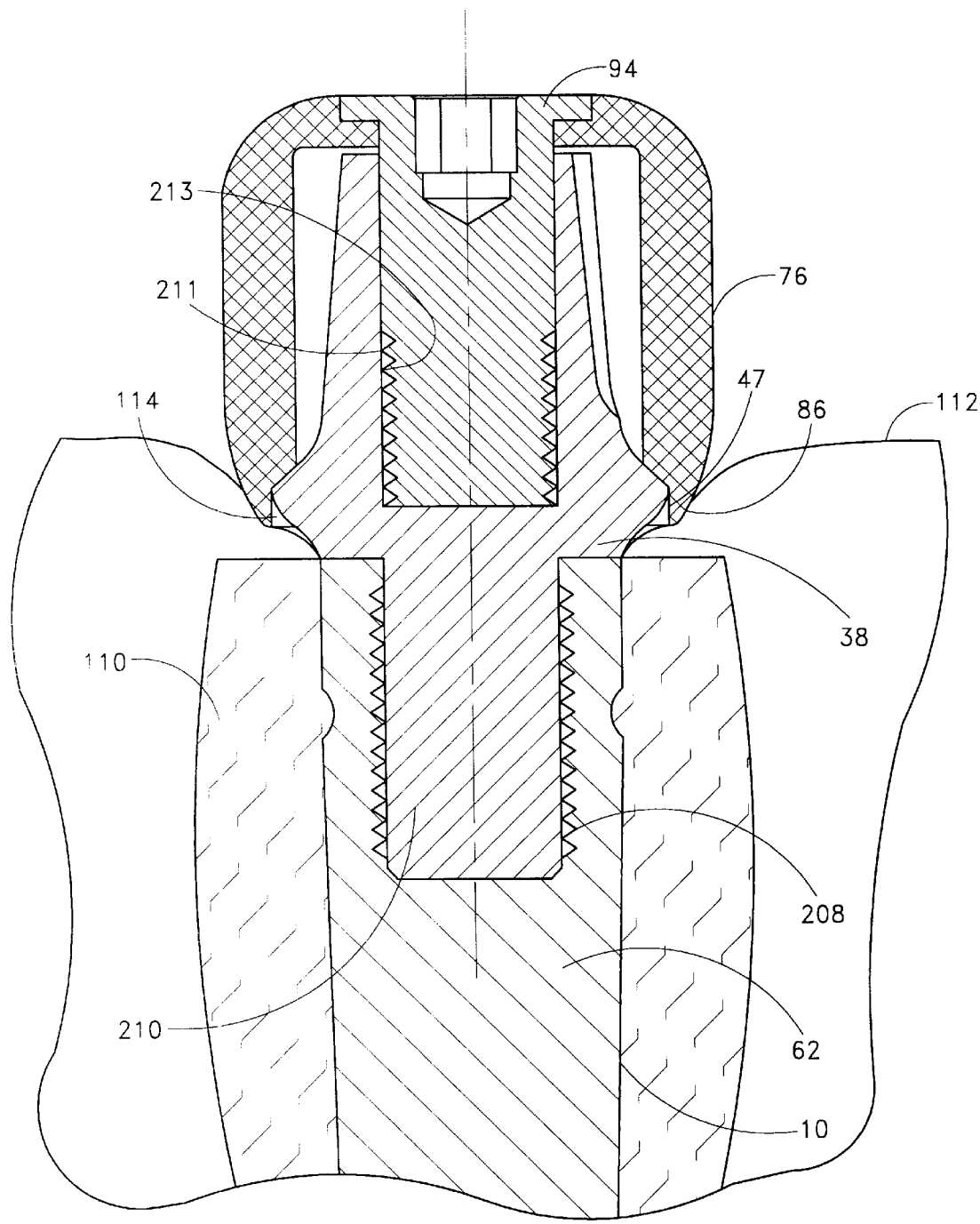
FIG. 11 is another embodiment of a heal in-place abutment system having certain features and advantages according to the present invention.

FIG. 11 illustrates another embodiment of a heal in-place abutment system having certain features and advantages according to the present invention. In this embodiment, the final abutment 38 includes a threaded post 208 that is configured to mate with a threaded chamber 210 formed in the implant 10. Accordingly, the final abutment 38 is not coupled to the implant 10 by a coupling screw 62. Instead, the abutment 38 is screwed directly into the implant 10. Another feature of this embodiment is that the healing cap screw 94 includes a threaded region 211 that is configured to engage threads 213 formed in the final abutment 38. One of the advantages of this arrangement is that it eliminates the need for a coupling screw. Moreover, the final abutment 39 doesn't need anti-rotation means such as a hexagonal protrusion or recess.

Figure 12:
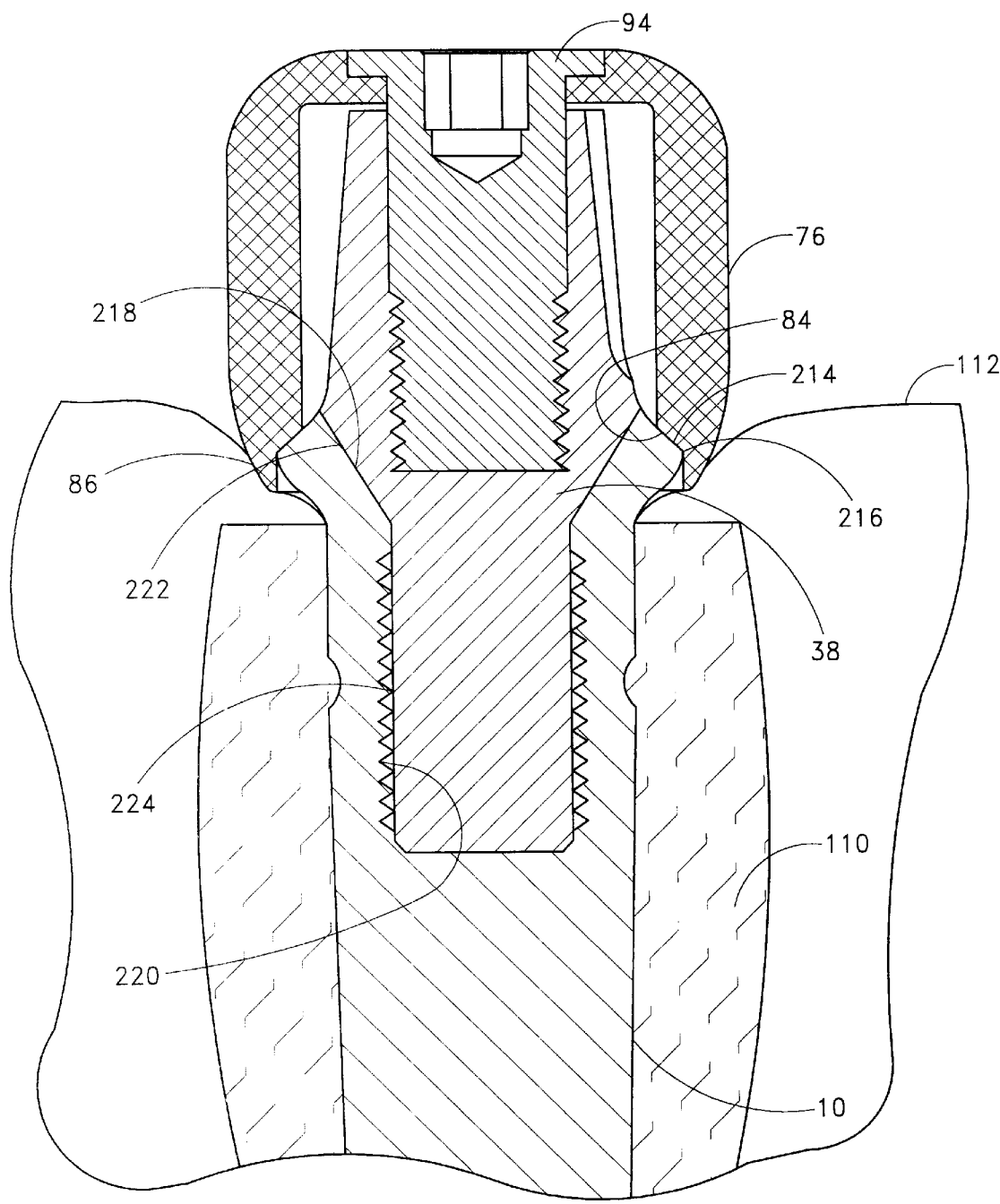
FIG. 12 is yet another embodiment of a heal in-place abutment system having certain features and advantages according to the present invention.

FIG. 12 illustrates yet another embodiment of a heal in-place abutment system having certain features and advantages according to the present invention. In this embodiment, the implant 10 is a conventional implant that is configured to be placed supra-crestally (i.e., the top surface 24 of the implant 10 is positioned above the crest of the jawbone). The implant 10 includes a flanged surface 214, which includes a shoulder 216. The internal socket 28 includes a sloped region 218 and a threaded region 202. The final abutment 38 includes a sloped surface 222 and a threaded region 224 configured to mate with the internal socket 28 of the implant.

The healing cap 76 is configured such that the base surface 84 rests against the flanged surface 214 of the implant 10. Correspondingly, the tissue retraction flange 86 is configured such that it extends beyond the shoulder 216 of the implant 10. As with the previous embodiment, the healing cap screw 94 is configured to screw directly into the final abutment 38.

Figure 13:
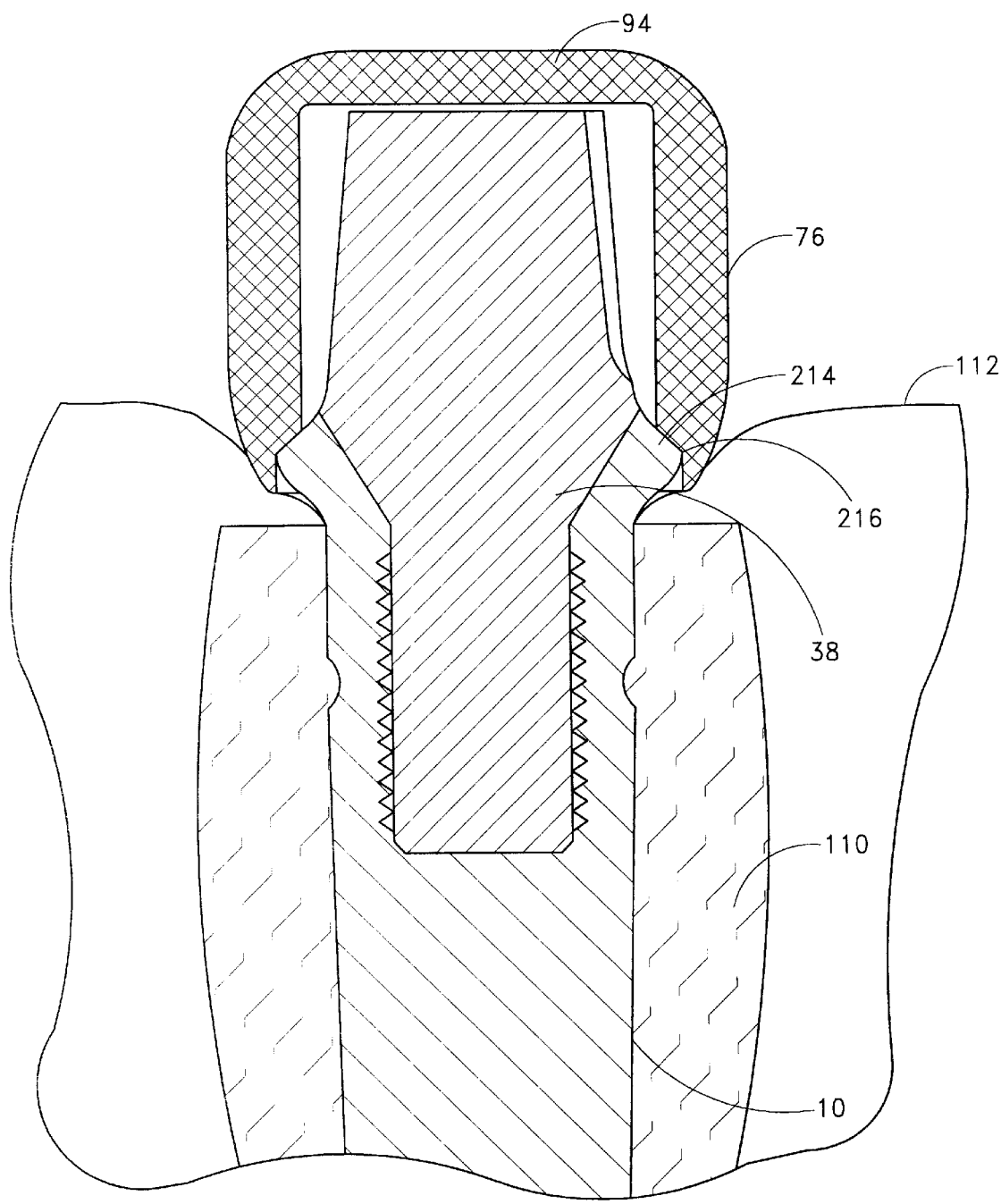
FIG. 13 is still yet another embodiment of a heal in-place abutment system having certain features and advantages according to the present invention.

FIG. 13 illustrates still yet another embodiment of a heal in-place abutment system having certain features and advantages according to the present invention. As with the previous embodiment, the final abutment 38 is configured such that it can be screwed directly into the implant 10. Moreover, the implant 10 includes a flanged surface 214 and a shoulder 216. However, in this embodiment the healing cap 76 is configured to be temporary attached by an adhesive, such as, for example cement. This arrangement, therefore, does not include a healing cap screw 94 and, thus, uses less components.

Certain objects and advantages of the invention have been described above for the purpose of summarizing the invention and the advantages achieved over the prior art. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Furthermore, although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

I claim:

1. A prosthodontic assembly for installing a prosthetic tooth, the prosthodontic assembly comprising:
   a dental implant and abutment combination that includes an implant body portion and an abutment portion, the implant body portion located at a distal end of the combination and configured to lie at least partially below a crest of a patient's jawbone, the abutment portion located at a proximate end of the combination and configured to lie at least partially above the crest of the patient's jawbone, the abutment portion comprising a flared portion, a shoulder portion and a final restoration portion, the shoulder portion lying between the flared portion and the final restoration portion,
   a healing cap including a body portion having a proximal and a distal end, the body portion defining an inner cavity which is sized and adapted so that the healing cap fits over the final restoration portion, the healing cap further including a tissue retraction flange at the distal end that extends below the shoulder portion when the healing cap is coupled to the abutment portion.

2. An assembly as in claim 1, wherein the tissue retraction flange also extends away from the flared portion.

3. An assembly as in claim 2, wherein a gap is formed between the tissue retraction flange and the flared portion.

4. An assembly as in claim 1, wherein the body portion of the healing cap includes a base portion that is configured to rest at least partially on the shoulder portion of the abutment portion.

5. An assembly as in claim 1, wherein the healing cap is coupled to the abutment portion by an adhesive.

6. An assembly as in claim 1, further including a healing cap screw having a threaded lower portion, the healing cap screw being configured to pass through a first opening of the healing cap and to couple the healing cap to the abutment portion.

7. An assembly as in claim 6, wherein the implant body portion includes a bore with a threaded section and the abutment portion includes a threaded post configured to engaged the threaded section and couple the abutment portion to the implant body portion.

8. An assembly as in claim 6, wherein the first opening includes a first portion having a first diameter and second portion having a second diameter, the second diameter being smaller than the first diameter, the healing cap screw including a head configured to fit within the first portion and a groove having a diameter smaller than the second diameter, the healing cap screw being press fitted into the first opening such that the second portion surrounds the groove and the head lies within the first portion, the healing cap screw being free to rotate with respect to the healing cap.

9. An assembly as in claim 1, wherein the flared portion and the shoulder portion of the abutment portion are integrally formed with the body portion.

10. An assembly as in claim 9, wherein the final restoration portion is a separate piece of the abutment portion and includes a threaded post that is configured to engage a threaded section of a bore that extends through the shoulder portion and flared portion into the body portion.

11. An assembly as in claim 1, wherein the abutment portion includes a distal end configured to be secured to the implant body portion and further including an indexing boss or recess formed therein for interlockingly engaging an indexing boss or recess formed on a proximal end of the implant body portion, the abutment portion further including a central bore that extends completely through the abutment portion; the assembly further including a coupling screw that includes a head and a threaded lower section, the coupling screw being configured to pass through the central bore of the abutment and to engage the threaded section of the implant so that the abutment portion can be coupled to the implant body portion.

12. An assembly as in claim 11, wherein the head portion of the coupling screw also includes a threaded section and the assembly further includes a healing cap screw having a threaded lower portion, the healing cap screw being configured to pass through a first opening of the healing cap and to engage the threaded section of the coupling screw.

13. An assembly as in claim 12, wherein the first opening includes a first portion having a first diameter and second portion having a second diameter, the second diameter being smaller than the first diameter, the healing cap screw including a head configured to fit within the first portion and a groove having a diameter smaller than the second diameter, the healing cap screw being press fitted into said healing cap such that the second portion surrounds the groove and the head lies within the first portion, the healing cap screw being free to rotate with respect to the healing cap.

14. An assembly as in claim 11, wherein the indexing boss or recess formed on the proximal end of the implant body portion comprises an internal cavity, the internal cavity comprising an interlock chamber, a post-receiving chamber and a threaded chamber, the interlock chamber having a cylindrical portion and three semi-circular channels arranged around a periphery of the cylindrical portion, the threaded chamber including threads and being located below the post-receiving chamber, which lies below the interlock chamber.

15. An assembly as in claim 11, wherein the indexing boss or recess formed on the proximal end of the implant body portion comprises a hexagonal boss.

16. An assembly as in claim 11, wherein the final restoration portion includes a plurality of grooves.

17. An assembly as in claim 1, wherein the healing cap is formed from a polymer.

18. An assembly as in claim 1, wherein the healing cap is formed from the group consisting polyester, nylon and combinations thereof.

19. An assembly as in claim 1, wherein the healing cap is white.

20. An assembly as in claim 1, wherein the healing cap has a color that is substantially the same a natural tooth.

21. An assembly as in claim 1, wherein the abutment portion and the healing cap have round cross-sections.

22. An assembly as in claim 1, wherein the abutment portion and the healing cap have non-round cross-sections.

23. A method for installing a prosthetic tooth, comprising the steps of:
   inserting a distal end of a body portion of a dental implant and abutment combination into a patient's jawbone during a first stage surgery;
   coupling a healing cap to an abutment portion of the combination, during first stage surgery, such that a tissue retraction flange of the healing cap extends below a shoulder portion of the abutment portion,
   removing the healing cap from the abutment portion during a second stage surgery, taking an impression of the combination during the second stage surgery after the healing cap has been removed from the abutment portion.

24. A method as in claim 23, wherein the step of coupling a healing cap to an abutment portion of the combination further includes using an adhesive to couple the healing cap to the abutment portion.

25. A method as in claim 24, wherein the step of coupling a healing cap to an abutment portion of the combination, further includes using a healing cap screw to couple the healing cap to the abutment portion.

26. A method as in claim 24, further including the step of threading a threaded post of the abutment portion into a threaded section of a bore of the implant body portion.

27. A method as in claim 24, further including the step of attaching the abutment portion to the implant body portion with a coupling screw that extends through a first bore, which extends completely through the abutment portion.

28. A method as in claim 27, wherein the step of coupling a healing cap to an abutment portion of the combination includes engaging a healing cap screw with a threaded section of a head portion of the coupling screw.

29. A healing cap for combination with a dental implant in a method of installing a prosthetic tooth, the healing cap comprising:
   a body having a proximal end, a distal end, and a cavity thereon, sized and adapted such that the distal end will fit over an abutment, and into a mounted position with respect to the abutment, the abutment having a radially outwardly extending shoulder;
   the body further comprising a tissue retraction surface, which extends distally of the shoulder when the body in the mounted position.

30. A healing cap as in claim 29, wherein the tissue retraction surface is on a distally extending tissue retraction flange on the healing cap.

31. A healing cap as in claim 30, wherein the tissue retraction flange also extends axially away from the abutment.

32. A healing cap as in claim 31, wherein a gap is formed between the tissue retraction flange and the abutment.

33. A healing cap as in claim 29, wherein the body includes a base portion that is configured to rest at least partially on the shoulder of the abutment.

34. A healing cap as in claim 29, wherein the healing cap is coupled to the abutment by an adhesive.

35. A healing cap as in claim 29, wherein the healing cap includes a first opening sized and adapted such that a healing cap screw having a threaded lower portion can pass through the first opening and couple the healing cap to the abutment.

36. A healing cap as in claim 35, wherein the first opening includes a first portion having a first diameter and second portion having a second diameter, the second diameter being smaller than the first diameter, the healing cap screw including a head configured to fit within the first portion and a groove having a diameter smaller than the second diameter, the healing cap screw being press fitted into the first opening such that the second portion surrounds the groove and the head lies within the first portion, the healing cap screw being free to rotate with respect to the healing cap.

37. A healing cap as in claim 29, wherein the healing cap is formed from a polymer.

38. A healing cap as in claim 29, wherein the healing cap is formed from the group consisting polyester, nylon and combinations thereof.

39. A healing cap as in claim 29, wherein the healing cap is white.

40. A healing cap as in claim 29, wherein the healing cap has a color that is substantially the same a natural tooth.

41. A healing cap as in claim 29, wherein the abutment and the healing cap have round cross-sections.

42. A healing cap as in claim 29, wherein the abutment portion and the healing cap have non-round cross-sections.

* * * * *